United States Patent
Kelin et al.

(10) Patent No.: US 9,546,860 B2
(45) Date of Patent: Jan. 17, 2017

(54) METHOD AND SYSTEM FOR CONTACTLESS DIMENSIONAL MEASUREMENT OF ARTICLES

(71) Applicant: MediaTek Singapore Pte. Ltd., Singapore (SG)

(72) Inventors: Timur Kelin, Cambourne (GB); Cyril Valadon, Letchworth Garden (GB)

(73) Assignee: MEDIATEK SINGAPORE PTE. LTD., Singapore (SG)

( * ) Notice: Subject to any disclaimer, the term of this patent is extended or adjusted under 35 U.S.C. 154(b) by 0 days.

(21) Appl. No.: 14/690,416

(22) Filed: Apr. 18, 2015

(65) Prior Publication Data

US 2016/0305765 A1 Oct. 20, 2016

(51) Int. Cl.
| | |
|---|---|
| *G01B 11/00* | (2006.01) |
| *G01B 11/02* | (2006.01) |
| *G01B 11/25* | (2006.01) |
| *G01N 21/956* | (2006.01) |
| *G01N 21/64* | (2006.01) |

(52) U.S. Cl.
CPC ........... *G01B 11/02* (2013.01); *G01B 11/2522* (2013.01); *G01N 21/6456* (2013.01); *G01N 21/956* (2013.01)

(58) Field of Classification Search
CPC . G01B 11/2522; G01B 11/02; G01N 21/6456; G01N 21/956; H04N 5/23238

USPC ............. 356/614–625; 382/1, 7, 65; 348/87, 348/211.11, 46, 118, 61; 438/34, 135
See application file for complete search history.

(56) References Cited

U.S. PATENT DOCUMENTS

| | | | | |
|---|---|---|---|---|
| 5,259,043 | A | * | 11/1993 | Concannon .......... G02B 6/0005 250/208.1 |
| 6,252,241 | B1 | * | 6/2001 | Sarussi ..................... H04N 1/10 250/234 |
| 7,508,509 | B2 | | 3/2009 | Lehtikoski et al. |
| 2007/0121122 | A1 | * | 5/2007 | Kaltenbach ............ G01B 11/00 356/625 |
| 2009/0022368 | A1 | * | 1/2009 | Matsuoka ............... B60K 35/00 382/103 |
| 2011/0164124 | A1 | * | 7/2011 | Hizume ............. G01N 21/6456 348/61 |
| 2012/0224052 | A1 | | 9/2012 | Bae |
| 2013/0314503 | A1 | * | 11/2013 | Nix ..................... G06K 9/00805 348/46 |
| 2015/0049345 | A1 | * | 2/2015 | Miyagawa ........... G01B 11/002 356/625 |

* cited by examiner

*Primary Examiner* — Sang Nguyen (74) *Attorney, Agent, or Firm* — Han IP Corporation; Andy M. Han (57) ABSTRACT

Methods and systems for contactless optical measurement of geometrical dimensions of articles are disclosed herein. A system according to the present disclosure may implement an arrangement of one or more measured articles, two imaging setups, a reflecting surface and a reference object. Geometrical dimensions of the one or more measured articles may be derived from dimensions of images formed in the imaging setups.

17 Claims, 8 Drawing Sheets

METHOD AND SYSTEM FOR CONTACTLESS DIMENSIONAL MEASUREMENT OF ARTICLES

TECHNICAL FIELD

The inventive concept described herein is generally related to measurement systems and, more specifically, to techniques, schemes and implementations of contactless optical measurement.

BACKGROUND

Unless otherwise indicated herein, approaches described in this section are not prior art to the claims listed below and are not admitted to be prior art by inclusion in this section.

Contactless dimensional measurements of articles are essential when there is a demand for fast and inexpensive estimations of the geometrical dimensions, provided that access to the measured articles is limited or the articles are in motion. For these situations different types of optical systems are typically used. These systems are usually based on the measurement of the projections of the measured articles formed by the optical system with known characteristics. With known or measured distance from the elements of the optical system to the measured articles the geometrical dimensions of the projections are recalculated to the dimensions of the articles. When the distance to the measured articles is not known, however, its contactless estimation would require special equipment, namely different types of range finders including optical ones.

Many everyday applications require fast yet accurate contactless dimensional measurements including, for example, measurements of the parts of a body for placing orders with online clothes retailers or for slimming process assessment. The usage of the range finders or other special equipment in such applications is highly undesirable.

SUMMARY

The following summary is illustrative only and is not intended to be limiting in any way. That is, the following summary is provided to introduce concepts, highlights, benefits and advantages of the novel and non-obvious techniques described herein. Select implementations are further described below in the detailed description. Thus, the following summary is not intended to identify essential features of the claimed subject matter, nor is it intended for use in determining the scope of the claimed subject matter.

An objective of the present disclosure is to provide schemes, techniques, methods, apparatuses and systems for measurement of geometrical dimensions of an article without knowledge of a distance to the measured article. Advantageously, implementations of the present disclosure need not obtain a distance to a measured article, and may be implemented in hand-held platforms or solutions for measurement.

In one aspect, a method of measuring geometrical dimensions of articles may include: measuring optical properties of a first imaging setup; measuring optical properties of a second imaging setup; measuring geometrical dimensions of a reference object; arranging one or more measured articles including a first measured article, the second imaging setup, a reflective surface, the first imaging setup, and the reference object in such a way that the first measured article is located in a visual field of the second imaging setup, with a reflection of the first measured article in the reflective surface and a reflection of the reference object in the reflective surface located in a visual field of the first imaging setup; forming an image of the reflection of the first measured article and the reflection of the reference object in the first imaging setup; forming an image of the first measured article in the second imaging setup; measuring geometrical dimensions of the image formed in the first imaging setup; measuring geometrical dimensions of the image formed in the second imaging setup; and calculating geometrical dimensions of the first measured article.

In another aspect, a method of forming and measuring geometrical dimensions of images of reflections may include: setting an imaging device in a front view position in such a way that a reflection of one or more measured articles including a first measured article in a reflective surface and a reflection of a reference object in the reflective surface are located in a visual field of the imaging device; forming images of the reflection of the first measured article and the reflection of the reference object; and measuring geometrical dimensions of the formed images.

In yet another aspect, a method of forming and measuring geometrical dimensions of images of articles may include: setting an imaging device in a rear view position in such a way that a first measured article is located in a visual field of the imaging device; forming an image of the first measured article; and measuring geometrical dimensions of the formed image.

In one aspect, a system for measuring geometrical dimensions of one or more measured articles may include: a front view imaging setup, a rear view imaging setup, a reflective surface, and a reference object. The front view imaging setup, the rear view imaging setup, the reflective surface and the reference object may be arranged in such a way that a first measured article of the one or more measured articles is located in a visual field of the rear view imaging setup, while a reflection of the first measured article in the reflective surface and a reflection of the reference object in the reflective surface are located in a visual field of the front view imaging setup.

Other features and advantages of the present disclosure will become apparent from the following description of various implementations which refer to the accompanying drawings.

BRIEF DESCRIPTION OF THE DRAWINGS

The accompanying drawings are included to provide a further understanding of the disclosure, and are incorporated in and constitute a part of the present disclosure. The drawings illustrate implementations of the disclosure and, together with the description, serve to explain the principles of the disclosure. It is appreciable that the drawings are not necessarily in scale as some components may be shown to be out of proportion than the size in actual implementation in order to clearly illustrate the concept of the present disclosure.

DETAILED DESCRIPTION OF PREFERRED IMPLEMENTATIONS

Overview

The present disclosure may be described in terms of various functional components and various processing steps. It should be appreciated that such functional components may be realized by any number of hardware or structural components configured to perform the specified functions. For example, the present disclosure may employ various integrated components comprised of various electrical, mechanical and optical devices.

In addition, the present disclosure may be practiced in any integrated application. Such general applications and other details that will be apparent to those skilled in the art in light of the present disclosure are not described in detail herein. Further, it should be noted that while various components may be suitably coupled or connected to other components within exemplary devices, such connections and couplings may be realized by direct connection between components, or by connection through other components and devices located therebetween.

Figure 8:
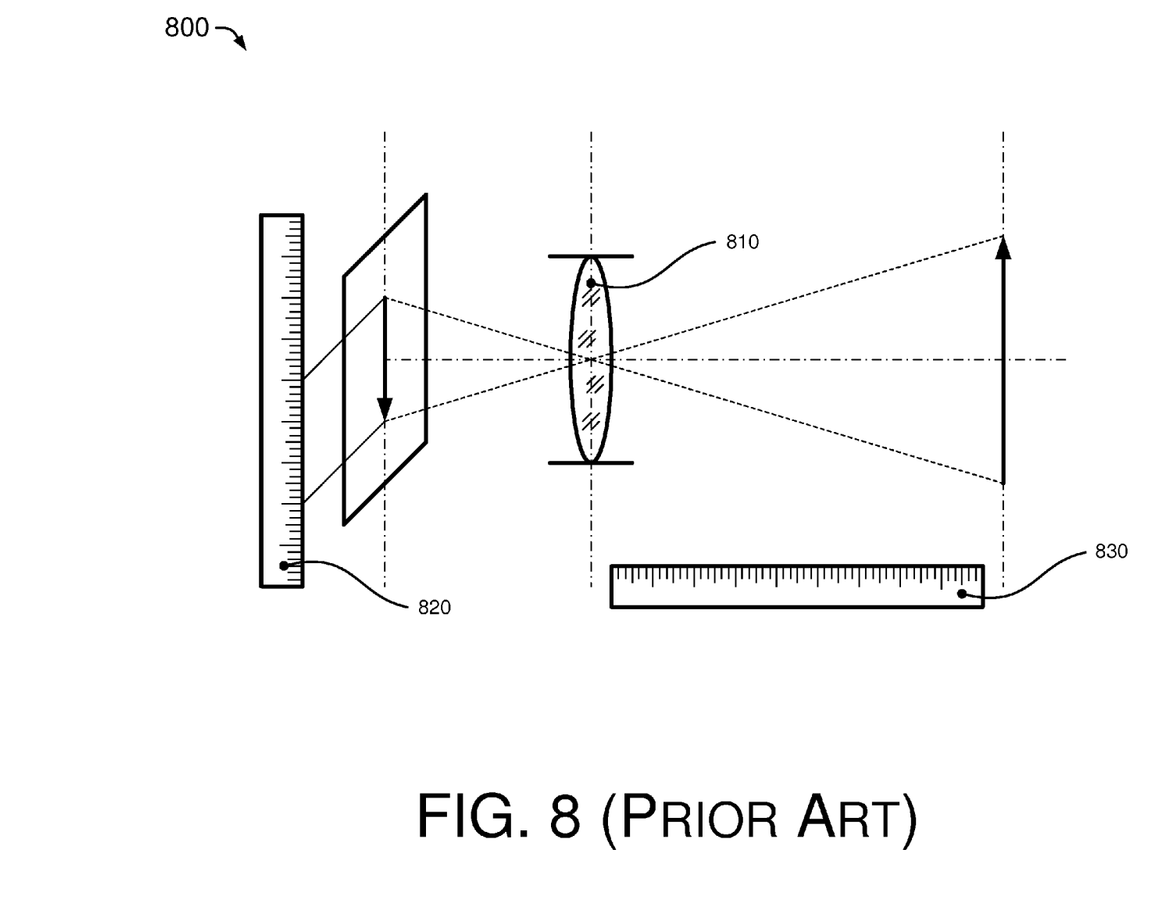
FIG. 8 is a block diagram showing a prior art measurement system.

Referring to FIG. 8, which shows a block diagram of a prior art measurement system 800. Prior art measurement system 800 includes an imaging setup (e.g., a camera of a mobile terminal) which includes a lens 810 with known characteristics, an image measurement subsystem 820, and a distance measurement subsystem 830. A method of measurement by prior art measurement system 800 typically includes the following steps: (1) recognizing an article image taken using the imaging setup; (2) measuring a size of the article image recognized in step (1) with image measurement subsystem 820; (3) measuring a distance between the article and the imaging setup with distance measurement subsystem 830; and (4) computing a real size of the article using the characteristics of the imaging setup (e.g., focal distance of lens 810 and the distance at which the image is formed), the size of the article image measured in step (2), and the distance between the object measured in step (3) and the imaging setup.

The operational sequence in prior art measurement system 800 includes measurement of a distance between the article and the camera which is done by distance measurement subsystem 830. There are many practical cases when this distance cannot be measured at all or measurement accuracy does not have the required level, e.g., when the measured article is moving or when there is limited access to the measured article.

In contrast, a primary advantage provided by methods and systems for measurement of geometrical dimensions in accordance with the present disclosure is its operation without the knowledge or direct measurement of the distance to the measured articles. That is, implementations in accordance with the present disclosure enable measurement of geometrical dimensions of articles without the need for means for distance measurement such as distance measurement subsystem 830. Such advantage may be achieved by the use of two imaging setups, a reflective surface (e.g., a mirror) and a reference object with known geometrical dimensions. In fact, in various implementations according to the present disclosure, a housing of one of the imaging setups or body of an assembly of two imaging setups may be used as a reference object.

Another feature of a proposed measurement system according to the present disclosure is the use of orientation detectors which are connected to the components of the measurement system. Measurements from the orientation detectors are taken into consideration when calculating the geometrical dimensions of the measured article(s) to compensate for the non-ideal spatial orientation (e.g., pitch and yaw) of the components of the measurement system. This may allow for a hand-held application for measurements.

Figure 1:
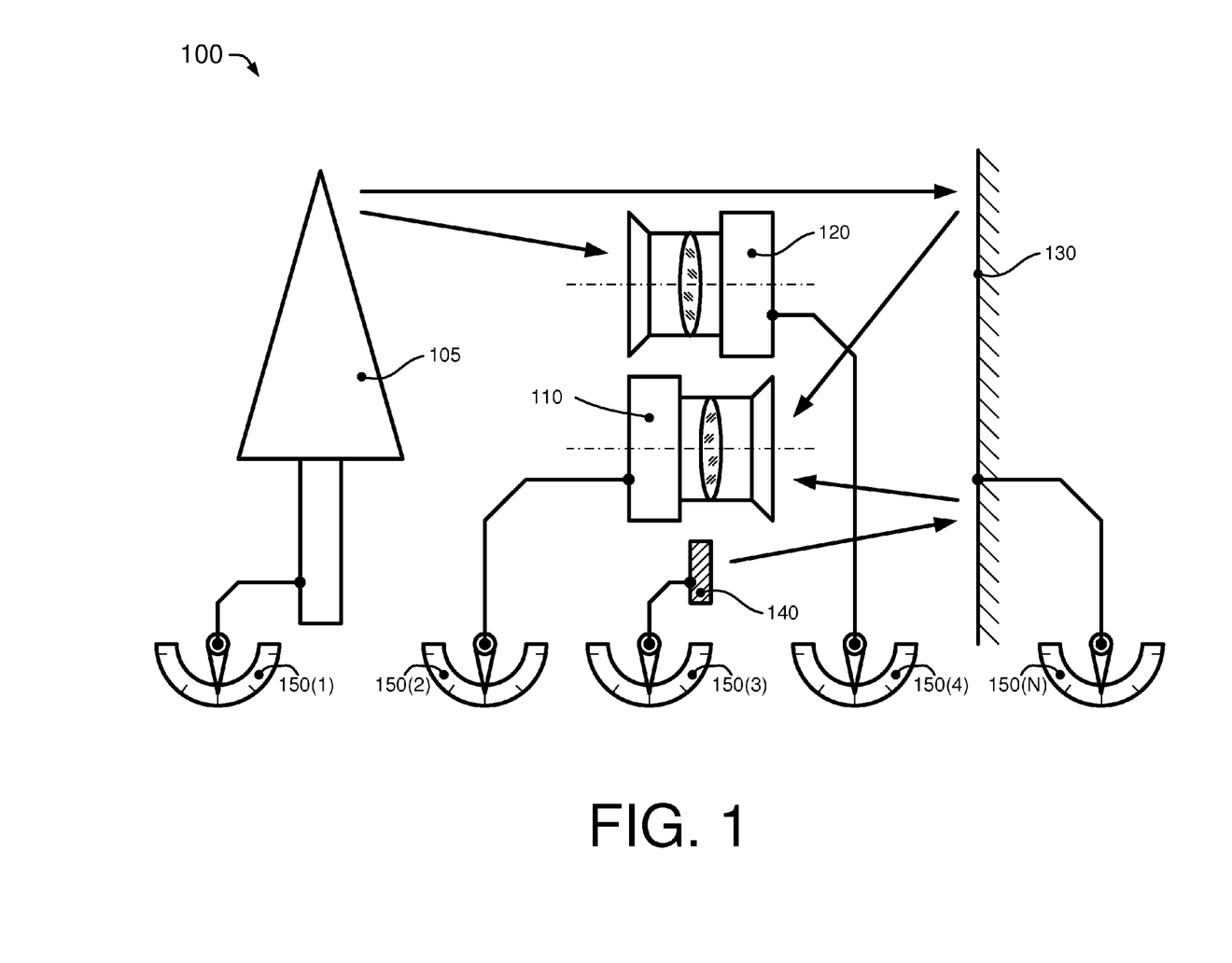
FIG. 1 is a block diagram showing an exemplary optical measurement system in accordance with at least some implementations of the present disclosure.
Figure 2:
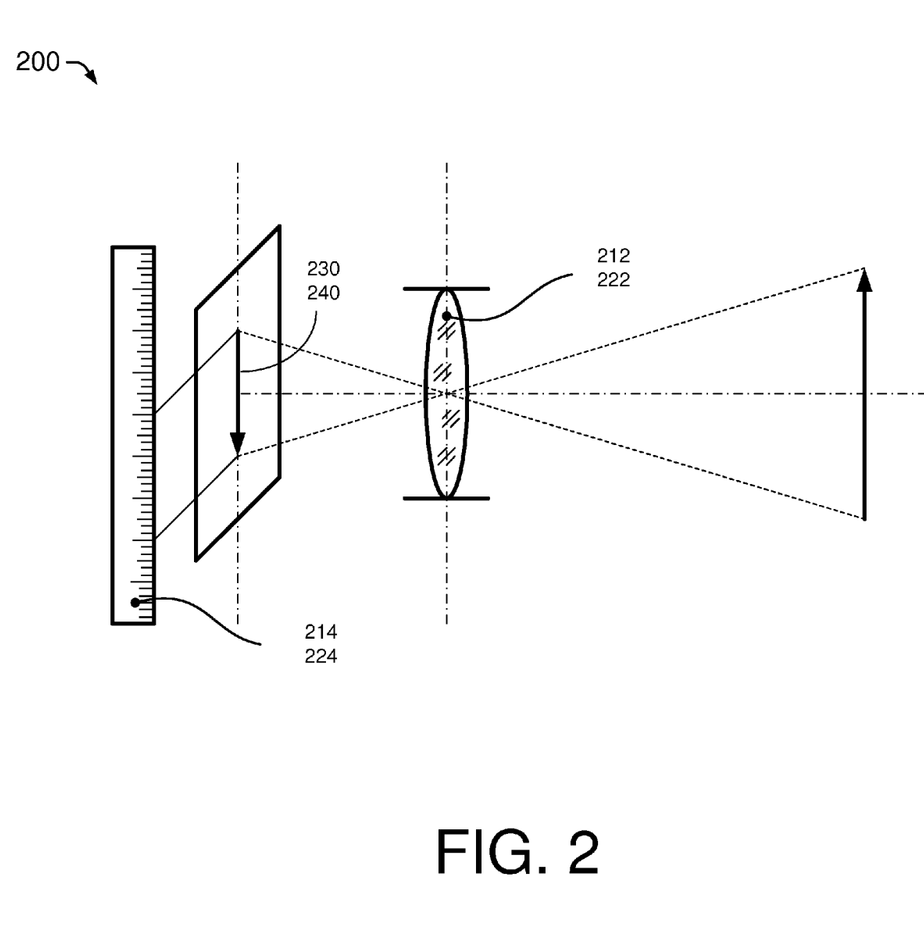
FIG. 2 is a block diagram showing an exemplary imaging setup of the exemplary measurement system of FIG. 1 in accordance with at least some implementations of the present disclosure.

FIG. 1 is a block diagram showing an exemplary optical measurement system 100 in accordance with at least some implementations of the present disclosure. FIG. 2 is a block diagram showing an exemplary imaging setup 200 of the exemplary measurement system 100 of FIG. 1 in accordance with at least some implementations of the present disclosure. The following description refers to FIG. 1 and FIG. 2.

Exemplary optical measurement system 100 may include a front view imaging setup 110, a rear view imaging setup 120, a reflective surface 130, and a reference object 140. Exemplary imaging setup 200 illustrates example components of each of front view imaging setup 110 and rear view imaging setup 120. As shown in FIG. 2, front view imaging setup 110 may include a lens 212 and an image measurement block 214, and rear view imaging setup 120 may include a lens 222 and an image measurement block 224.

Front view imaging setup 110 may form an image 230 through the lens 212 and then may measure the geometrical dimensions of the image 230 with the image measurement block 214. Rear view imaging setup 120 may form an image 240 through the lens 222 and then may measure the geometrical dimensions of the image 240 with the image measurement block 224.

Measurement of images may be accomplished by, for example, a charge-coupled device (CCD) or a complementary metal-oxide semiconductor (CMOS) pixel matrix.

In implementations according to the present disclosure, optical properties of front view imaging setup 110 and rear view imaging setup 120 are known or previously measured. Moreover, geometrical dimensions of reference object 140 are also known or previously measured.

To perform the measurement of geometrical dimensions of a first measured article 105, the first measured article 105, the front view imaging setup 110, the rear view imaging setup 120, the reflective surface 130, and the reference object 140 may be arranged in such a way that the first measured article 105 is located in the visual field of the rear view imaging setup 120, while the reflection of the first measured article 105 in the reflective surface 130 and the reflection of the reference object 140 in the reflective surface 130 are located in the visual field of the front view imaging setup 110. This may be achieved by changing the position and/or spatial orientation of one or more components of exemplary optical measurement system 100 as well as that of the first measured article 105.

An image of the first measured article 105 may be formed by the rear view imaging setup 120 through its lens 222. The dimensions of the image of the first measured article 105 may then be measured by the image measurement block 224 of the rear view imaging setup 120.

Images of the reflections may be formed by the front view imaging setup 110 through its lens 212. The dimensions of the images of the reflections of the first measured article 105 and the reference object 140 may then be measured by the image measurement block 214 of the front view imaging setup 110.

Having dimensions of the images of the first measured article 105 as well as the reflections of the first measured article 105 and the reference object 140, the geometrical dimensions of the first measured article 105 can be calculated. Exemplary calculations are provided below.

The spatial orientation of the components of exemplary optical measurement system 100 may be non-ideal, for example, having pitch and yaw, which gives an error in the geometrical measurements. To compensate for this, one or more of the components of exemplary optical measurement system 100 may be connected to one or more of orientation detectors 150(1)-150(N), where N is a positive integer greater than or equal to one. For instance, each, one or some of the first measured article 105, the front view imaging setup 110, the rear view imaging setup 120, the reflective surface 130 and the reference object 140 may be connected to orientation detectors 150(1)-150(N), respectively. Thus, to compensate for pitch and/or yaw in one or more components of exemplary optical measurement system 100, measurements from orientation detectors 150(1)-150(N) may be taken into consideration when calculating the geometrical dimensions of the first measured article 105.

In some implementations, some or all of front view imaging setup 110, rear view imaging setup 120 and reference object 140 may be mounted in a single assembly, thus making a major part of exemplary optical measurement system 100 easy to handle.

Figure 3:
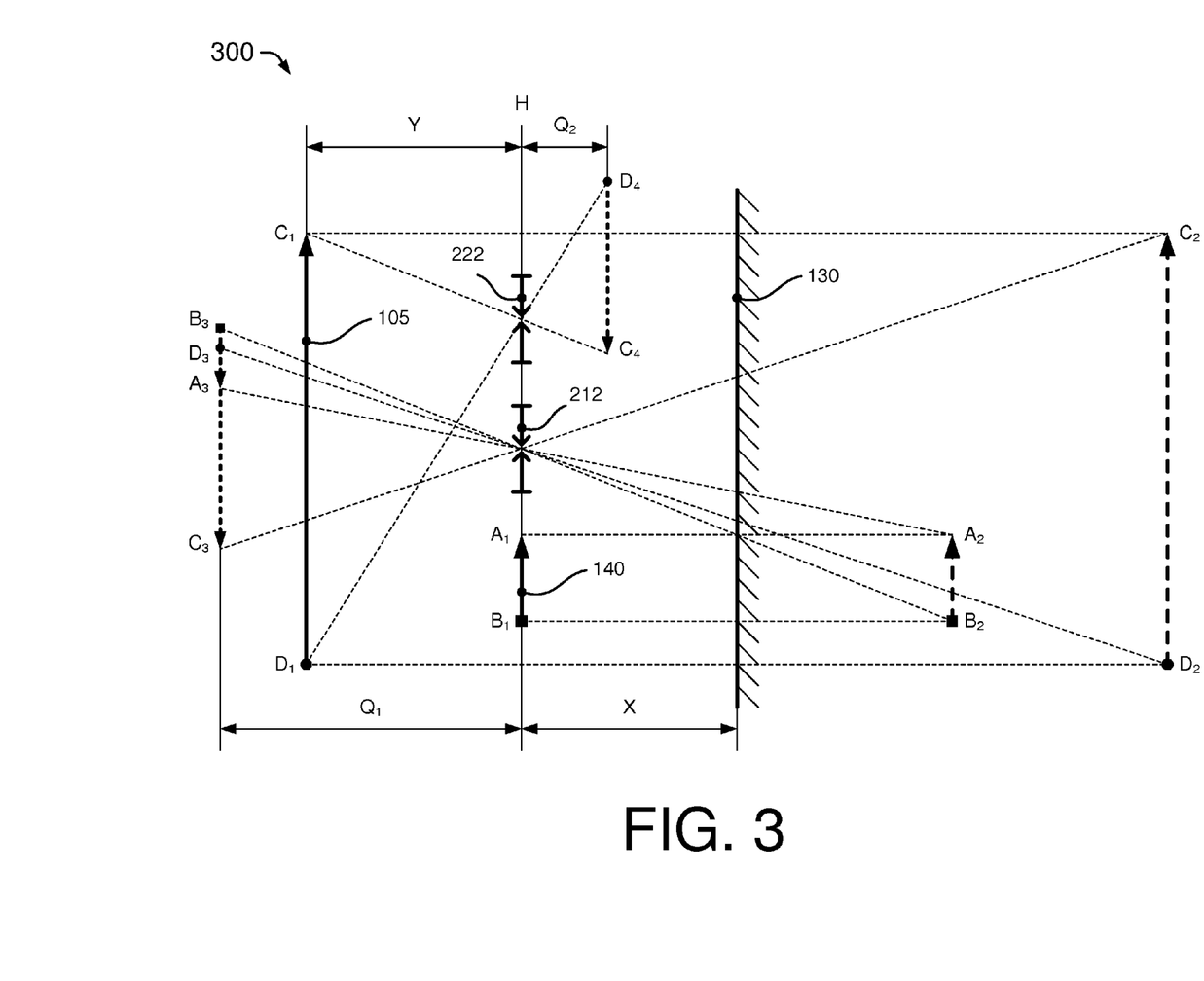
FIG. 3 is an optical diagram of an exemplary scenario showing exemplary ray path in the exemplary measurement system of FIG. 1 in accordance with at least some implementations of the present disclosure.

FIG. 3 is an optical diagram of an exemplary scenario 300 showing exemplary ray path in exemplary measurement system 100 of FIG. 1 in accordance with at least some implementations of the present disclosure.

For simplicity in description, lenses 212 and 222 are considered to be simple small aperture or pinhole "lenses". The images 230 and 240 are formed at respective distances Q1 and Q2 behind the respective lenses 212 and 222. Principal planes of lenses 212 and 222 are superimposed into a single plane H. The reference object 140 is also located within the plane H. The reflective surface 130 is flat (flat mirror) and is parallel to the plane H.

The length of the reflection of the reference object 140 projected through lens 212 of front view imaging setup 110 may be provided by Equation (1) as follows:

$$A_3B_3 = A_2B_2 \times \frac{Q_1}{2X} \qquad (1)$$

In Equation (1), $A_2B_2$ is the length of the reflection of reference object 140. It is equal to the length of reference object 140 which is $A_1B_1$ and is known. Additionally, $A_3B_3$ is the length of the projection measured by image measurement block 214 of front view imaging setup 110, and X is the distance from the plane H to the reflective surface 130.

The length of the reflection of the first measured article 105 projected through lens 212 may be provided by Equation (2) as follows:

$$C_3D_3 = C_2D_2 \times \frac{Q_1}{2X+Y} \qquad (2)$$

In Equation (2), $C_2D_2$ is the length of the reflection of the first measured article 105. It is equal to the length of the first measured article 105 $C_1D_1$ and needs to be determined. Additionally, $C_3D_3$ is the length of the projection measured by image measurement block 214 of front view imaging setup 110, and Y is the distance from the plane H to the first measured article 105.

Equation (3), shown below, may be obtained by combining Equation (1) and Equation (2), as follows:

$$C_1D_1 = C_2D_2 = C_3D_3 \times \frac{2X+Y}{Q_1} = \qquad (3)$$
$$\frac{C_3D_3}{Q_1} \times \left(\frac{A_2B_2}{A_3B_3} \times Q_1 + Y\right) = C_3D_3 \times \left(\frac{A_1B_1}{A_3B_3} + \frac{Y}{Q_1}\right)$$

The length of the image of the first measured article 105 projected through lens 222 of rear view imaging setup 120 may be provided by Equation (4) as follows:

$$C_4D_4 = C_1D_1 \times \frac{Q_2}{Y} \qquad (4)$$

In Equation (4), $C_1D_1$ is the length of the first measured article 105, which the dimension of interest. Moreover, $C_4D_4$ is the length of the projection measured by image measurement block 224 of rear view imaging setup 120.

Equation (5), shown below, may be obtained by combining Equations (3) and (4) and solving $C_1D_1$, as follows:

$$C_1D_1 = C_3D_3 \times \frac{A_1B_1}{A_3B_3} \times \frac{Q_1 \times C_4D_4}{Q_1 \times C_4D_4 - Q_2 \times C_3D_3} \qquad (5)$$

The calculated length of the first measured article 105, $C_1D_1$, is positive given the condition expressed by Inequality (6), as follows:

$$Q_1 \times C_4D_4 - Q_2 \times C_3D_3 \geq 0 \qquad (6)$$

Inequality (7), shown below, may be obtained by implementing Equations (2) and (4) into Inequality (6), as follows:

$$\frac{1}{Y} - \frac{1}{2X+Y} \geq 0 \qquad (7)$$

Inequality (7) is true for all of the practical cases.

The distance Y from the plane H to the first measured article 105 and the distance X+Y from the reflective surface 130 to the first measured article 105 may also be calculated.

If one or more additional measured articles, which may be a part of the first measured article 105, are located at the same distance Y from the plane H, their geometrical dimensions may be determined if the one or more additional measured articles are located in the visual field of the rear view imaging setup 120. Alternatively, if the one or more additional measured articles are located at the same distance X+Y from the reflective surface 130, their geometrical dimensions may be determined if the reflections of the one or more additional measured articles in the reflective surface 130 are located in the visual field of the front view imaging setup 110.

Similar calculations may be performed for optical camera lenses in places of lenses 212 and 222 with their additional optical characteristics (e.g., focal distances) taken into account.

Figure 4:
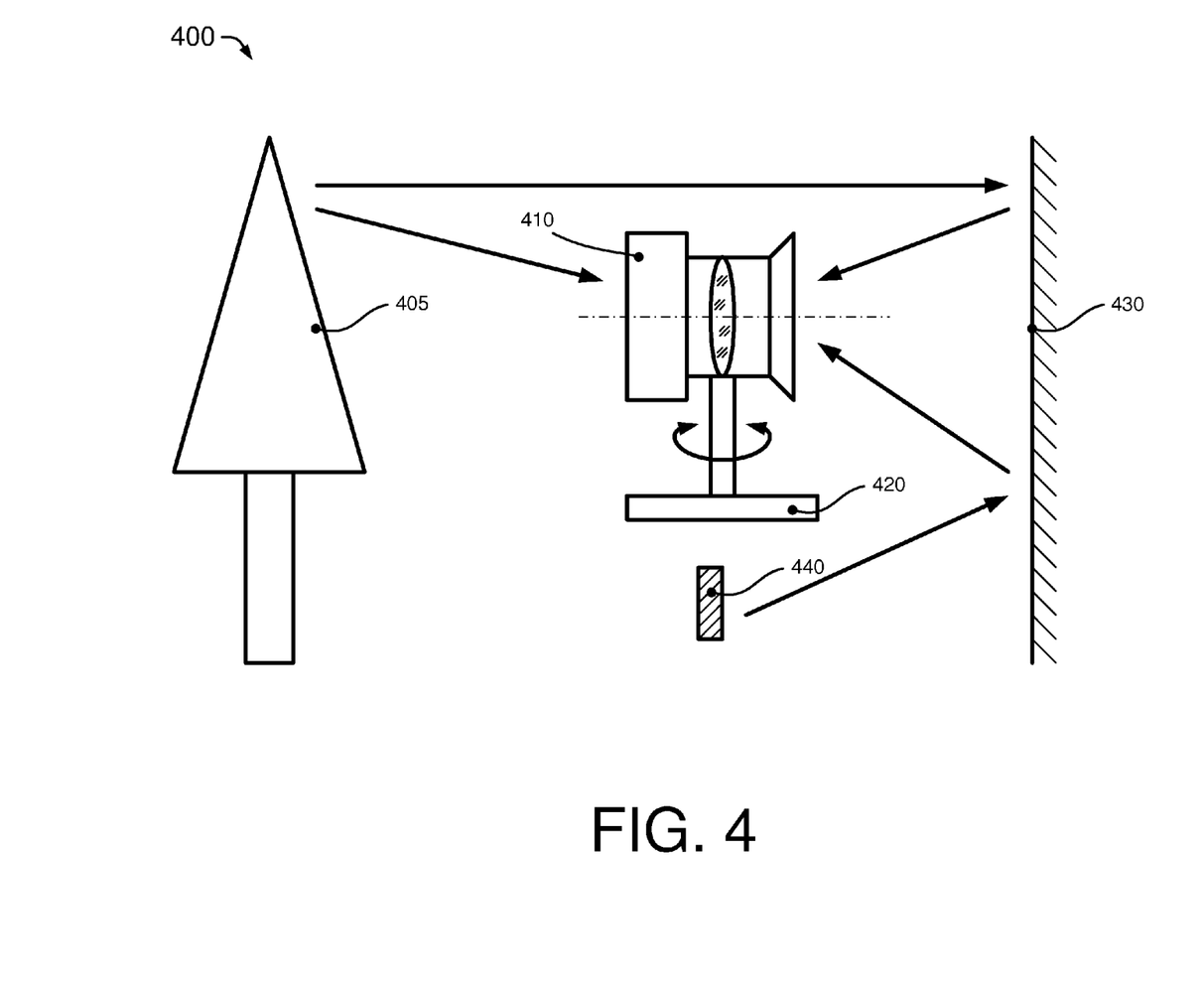
FIG. 4 is a block diagram showing an exemplary flexible mount of the imaging device for an exemplary measurement system in accordance with at least some implementations of the present disclosure.

FIG. 4 is a block diagram showing an exemplary flexible mount of the imaging device for an exemplary measurement system 400 in accordance with at least some implementations of the present disclosure.

Exemplary measurement system 400 may be similar to exemplary measurement system 100 of FIG. 1. Thus, in the interest of brevity, description of exemplary measurement system 400 is focused on differences between exemplary measurement system 400 and exemplary measurement system 100. As shown in FIG. 4, exemplary measurement system 400 may be equipped with an imaging device 410 connected to, coupled to or otherwise mounted on an imaging device mount 420. Imaging device 410 may have the capabilities of forming an image and measuring the geometrical dimensions of the image. Imaging device mount 420 may be set in a front view position. In this case imaging device 410 may have the functions and capabilities of front view imaging setup 110 as described above. Alternatively, imaging device mount 420 may be set in a rear view position. In this case imaging device 410 may have the functions and capabilities of rear view imaging setup 120 as described above. In some implementations, imaging device mount 420 may include a tripod with a rotating head.

Exemplary Implementations

In view of the above and FIG. 1-FIG. 4, a system for measuring geometrical dimensions of one or more measured articles may include: a front view imaging setup, a rear view imaging setup, a reflective surface, and a reference object. The front view imaging setup, the rear view imaging setup, the reflective surface and the reference object may be arranged in such a way that a first measured article of the one or more measured articles is located in a visual field of the rear view imaging setup, while a reflection of the first measured article in the reflective surface and a reflection of the reference object in the reflective surface are located in a visual field of the front view imaging setup.

In at least some implementations, at least one additional measured articles of the one or more measured articles may be located in the visual field of the rear view imaging setup.

In at least some implementations, a reflection of at least one additional measured article of the one or more measured articles in the reflective surface may be located in the visual field of the front view imaging setup.

In at least some implementations, the front view imaging setup may be connected to a spatial orientation detector. Additionally or alternatively, the rear view imaging setup may be connected to a spatial orientation detector. Additionally or alternatively, the reflective surface is connected to a spatial orientation detector. Additionally or alternatively, the reference object is connected to a spatial orientation detector. Additionally or alternatively, each of the one or more measured articles is connected to a respective spatial orientation detector.

In at least some implementations, the front view imaging setup and the rear view imaging setup may be mounted in a single assembly. Additionally or alternatively, the front view imaging setup and the reference object are mounted in a single assembly. Additionally or alternatively, the rear view imaging setup and the reference object are mounted in a single assembly.

In at least some implementations, the front view imaging setup may include an imaging device and an imaging device mount on which the imaging device is mounted. The imaging device mount may be set to a front view position.

In at least some implementations, the rear view imaging setup may include an imaging device and an imaging device mount on which the imaging device is mounted. The imaging device mount may be set to a rear view position.

Figure 5:
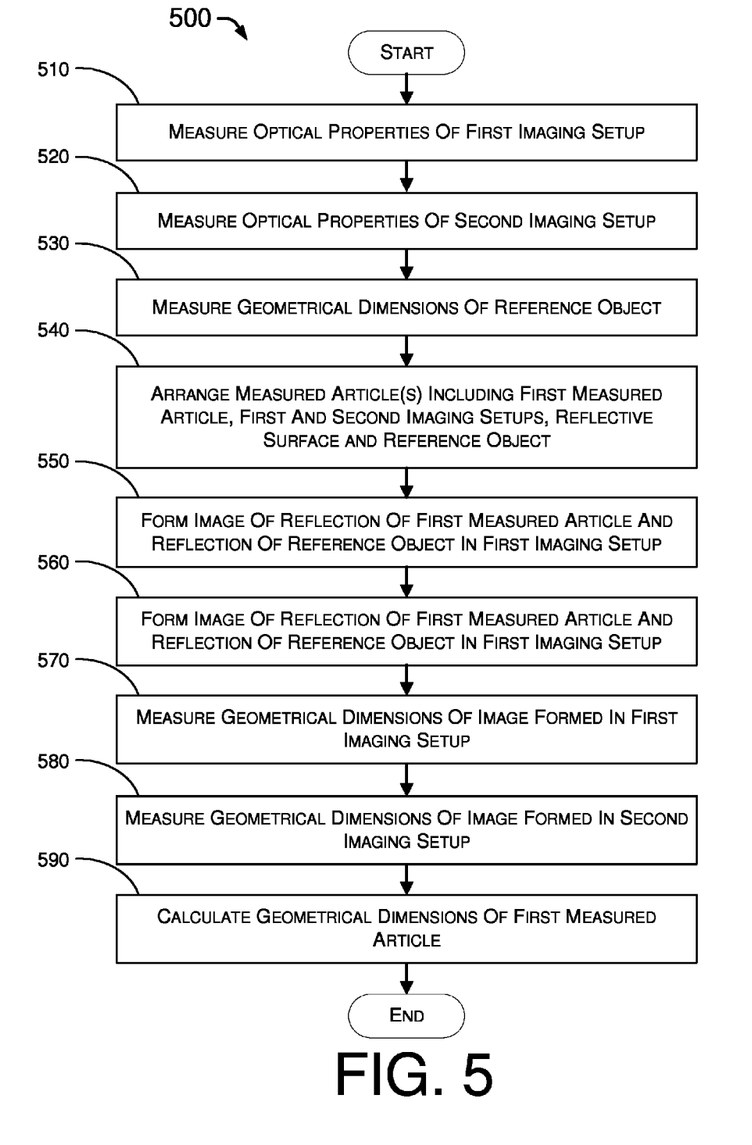
FIG. 5 is a flowchart showing an exemplary process in accordance with at least some implementations of the present disclosure.

FIG. 5 is a flowchart showing an exemplary process 500 in accordance with at least some implementations of the present disclosure.

Exemplary process 500 may include one or more operations, actions, or functions as illustrated by one or more of blocks 510-590. Although illustrated as discrete blocks, various blocks may be divided into additional blocks, combined into fewer blocks, or eliminated, depending on the desired implementation. Exemplary process 500 may be implemented by exemplary measurement system 100 or exemplary measurement system 400. For illustrative purposes, the operations described below with respect to exemplary process 500 are performed by components of exemplary measurement system 100. Exemplary process 500 may begin at block 510.

Block 510 (Measure Optical Properties Of First Imaging Setup) may involve measuring optical properties of a first imaging setup. In some implementations, any suitable instrument, system or mechanism capable of measuring optical properties of the first imaging setup may be used to measure the optical properties of the first imaging setup in lieu of or in addition to exemplary measurement system 100. Block 510 may be followed by block 520.

Block 520 (Measure Optical Properties Of Second Imaging Setup) may involve measuring optical properties of a second imaging setup. In some implementations, any suitable instrument, system or mechanism capable of measuring optical properties of the second imaging setup may be used to measure the optical properties of the second imaging setup in lieu of or in addition to exemplary measurement system 100. Block 520 may be followed by block 530.

Block 530 (Measure Geometrical Dimensions Of Reference Object) may involve measuring geometrical dimensions of a reference object. In some implementations, any suitable instrument, system or mechanism capable of measuring geometrical dimensions of the reference object may be used to measure the geometrical dimensions of the reference object in lieu of or in addition to exemplary measurement system 100. Block 530 may be followed by block 540.

Block 540 (Arrange Measured Article(s) Including First Measured Article, First And Second Imaging Setups, Reflective Surface and Reference Object) may involve arranging one or more measured articles (including a first measured article), the second imaging setup, a reflective surface, the first imaging setup, and the reference object in such a way that the first measured article is located in a visual field of the second imaging setup, with a reflection of the first measured article in the reflective surface and a reflection of the reference object in the reflective surface located in a visual field of the first imaging setup. Block 540 may be followed by block 550.

Block 550 (Form Image Of Reflection Of First Measured Article And Reflection Of Reference Object In First Imaging Setup) may involve exemplary measurement system 100 forming an image of the reflection of the first measured article and the reflection of the reference object in the first imaging setup. Block 550 may be followed by block 560.

Block 560 (Form Image Of Reflection Of First Measured Article And Reflection Of Reference Object In First Imaging Setup) may involve exemplary measurement system 100 forming an image of the first measured article in the second imaging setup. Block 560 may be followed by block 570.

Block 570 (Measure Geometrical Dimensions Of Image Formed In First Imaging Setup) may involve exemplary measurement system 100 measuring geometrical dimensions of the image formed in the first imaging setup. Block 570 may be followed by block 580.

Block 580 (Measure Geometrical Dimensions Of Image Formed In Second Imaging Setup) may involve exemplary measurement system 100 measuring geometrical dimensions of the image formed in the second imaging setup. Block 580 may be followed by block 590.

Block 590 (Calculate Geometrical Dimensions Of First Measured Article) may involve calculating geometrical dimensions of the first measured article. In some implementations, any suitable computing device, instrument, system or mechanism capable of calculating the geometrical dimensions of the first measured article may be used to calculate the geometrical dimensions of the first measured article.

In at least some implementations, the arranging of the one or more measured articles may further involve arranging one or more additional measured articles and the second imaging setup in such a way that the one or more additional measured articles are located in the visual field of the second imaging setup.

In at least some implementations, the arranging of the one or more measured articles may further involve arranging one or more additional measured articles, the reflective surface and the first imaging setup in such a way that reflections of the one or more additional measured articles are located in the visual field of the first imaging setup.

In at least some implementations, the calculating of the geometrical dimensions may further involve exemplary measurement system 100 detecting a spatial orientation of the first imaging setup.

In at least some implementations, the calculating of the geometrical dimensions may further involve exemplary measurement system 100 detecting a spatial orientation of the second imaging setup.

In at least some implementations, the calculating of the geometrical dimensions may further involve exemplary measurement system 100 detecting a spatial orientation of the reference object.

In at least some implementations, the calculating of the geometrical dimensions may further involve exemplary measurement system 100 detecting a spatial orientation of the reflective surface.

In at least some implementations, the calculating of the geometrical dimensions may further involve exemplary measurement system 100 detecting spatial orientations of the one or more measured articles.

In at least some implementations, the calculating of the geometrical dimensions may further involve calculating distances to the one or more measured articles.

In at least some implementations, the first imaging setup may be a front view imaging setup, and the second imaging setup may be a rear view imaging setup.

Figure 6:
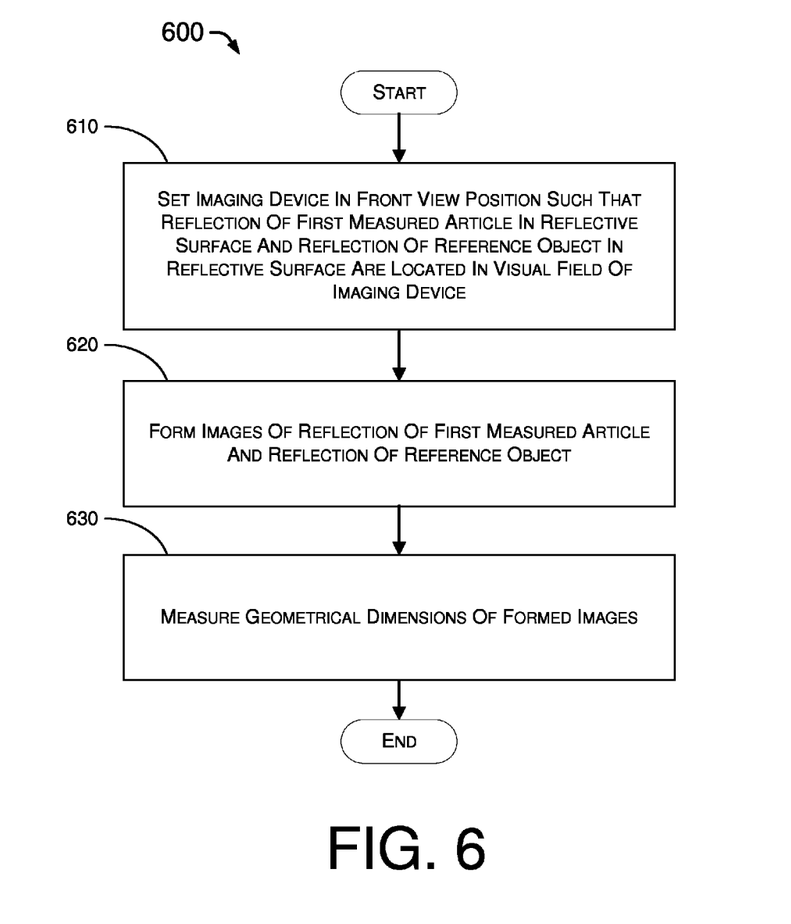
FIG. 6 is a flowchart showing an exemplary process in accordance with at least some implementations of the present disclosure.

FIG. 6 is a flowchart showing an exemplary process 600 in accordance with at least some implementations of the present disclosure.

Exemplary process 600 may include one or more operations, actions, or functions as illustrated by one or more of blocks 610, 620 and 630. Although illustrated as discrete blocks, various blocks may be divided into additional blocks, combined into fewer blocks, or eliminated, depending on the desired implementation. Exemplary process 600 may be implemented by exemplary measurement system 100 or exemplary measurement system 400. For illustrative purposes, the operations described below with respect to exemplary process 600 are performed by components of exemplary measurement system 100. Exemplary process 600 may begin at block 610.

Block 610 (Set Imaging Device In Front View Position Such That Reflection Of First Measured Article In Reflective Surface And Reflection Of Reference Object In Reflective Surface Are Located In Visual Field Of Imaging Device) may involve exemplary measurement system 100 setting an imaging device in a front view position in such a way that a reflection of one or more measured articles including a first measured article in a reflective surface and a reflection of a reference object in the reflective surface are located in a visual field of the imaging device. Block 610 may be followed by block 620.

Block 620 (Form Images Of Reflection Of First Measured Article And Reflection Of Reference Object) may involve exemplary measurement system 100 forming images of the reflection of the first measured article and the reflection of the reference object. Block 620 may be followed by block 630.

Block 630 (Measure Geometrical Dimensions Of Formed Images) may involve exemplary measurement system 100 measuring geometrical dimensions of the formed images.

Figure 7:
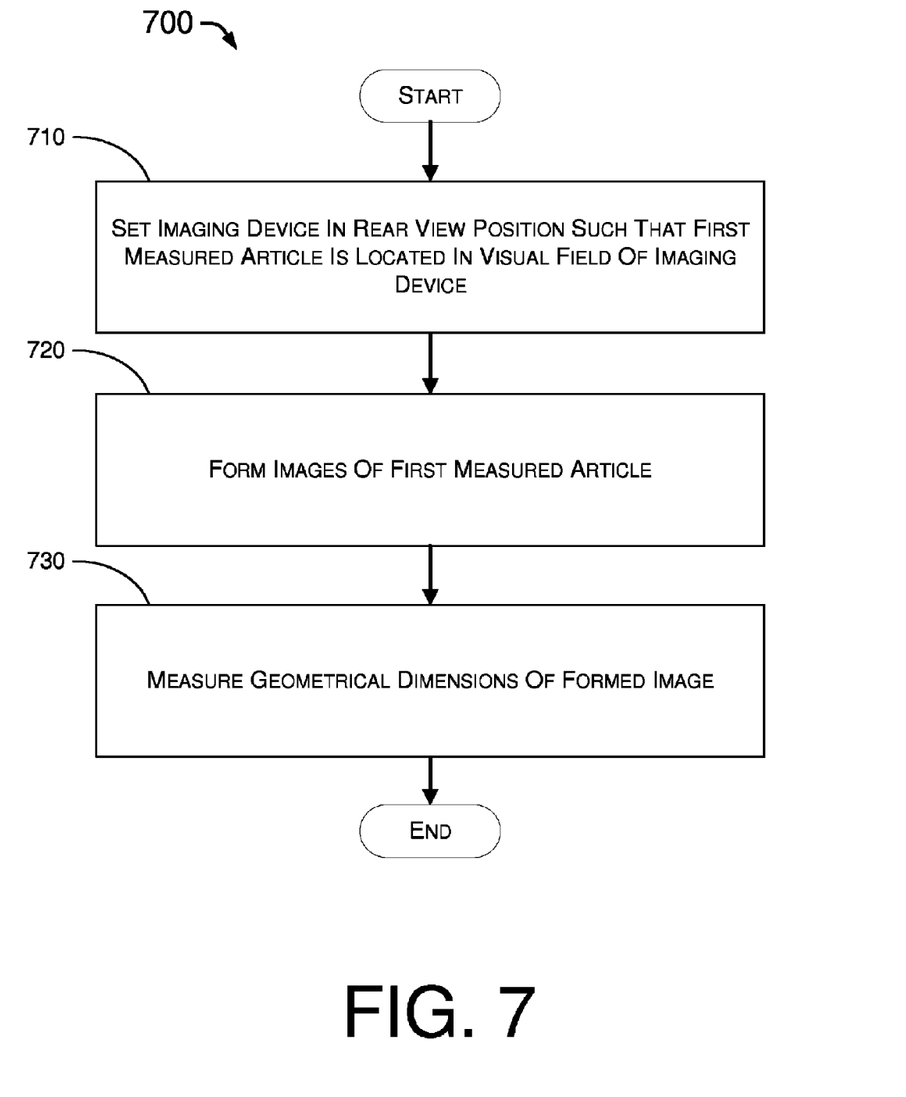
FIG. 7 is a flowchart showing an exemplary process in accordance with at least some implementations of the present disclosure.

FIG. 7 is a flowchart showing an exemplary process 700 in accordance with at least some implementations of the present disclosure.

Exemplary process 700 may include one or more operations, actions, or functions as illustrated by one or more of blocks 710, 720 and 730. Although illustrated as discrete blocks, various blocks may be divided into additional blocks, combined into fewer blocks, or eliminated, depending on the desired implementation. Exemplary process 700 may be implemented by exemplary measurement system 100 or exemplary measurement system 400. For illustrative purposes, the operations described below with respect to exemplary process 700 are performed by components of exemplary measurement system 100. Exemplary process 700 may begin at block 710.

Block 710 (Set Imaging Device In Rear View Position Such That First Measured Article Is Located In Visual Field Of Imaging Device) may involve exemplary measurement system 100 setting an imaging device in a rear view position in such a way that a first measured article is located in a visual field of the imaging device. Block 710 may be followed by block 720.

Block 720 (Form Images Of First Measured Article) may involve exemplary measurement system 100 forming an image of the first measured article. Block 720 may be followed by block 730.

Block 730 (Measure Geometrical Dimensions Of Formed Image) may involve exemplary measurement system 100 measuring geometrical dimensions of the formed image.

Additional Notes

The herein-described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Further, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Moreover, it will be understood by those skilled in the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various implementations of the present disclosure have been described herein for purposes of illustration, and that various modifications may be made without departing from the scope and spirit of the present disclosure. Accordingly, the various implementations disclosed herein are not intended to be limiting, with the true scope and spirit being indicated by the following claims.

What is claimed is:

1. A method of measuring geometrical dimensions of articles, comprising:
    arranging one or more measured articles including a first measured article, a first image setup, a second imaging setup, a reflective surface, and a reference object in such a way that the first measured article is located in a visual field of the second imaging setup, with a reflection of the first measured article in the reflective surface and a reflection of the reference object in the reflective surface located in a visual field of the first imaging setup;
    forming an image of the reflection of the first measured article and the reflection of the reference object in the first imaging setup, the first imaging setup comprising a first lens and a first image measurement device;
    forming an image of the first measured article in the second imaging setup, the second imaging setup comprising a second lens and a second image measurement device;
    measuring, using the first imaging setup, geometrical dimensions of the image formed in the first imaging setup;
    measuring, using the second imaging setup, geometrical dimensions of the image formed in the second imaging setup; and
    calculating geometrical dimensions of the first measured article based on measurements from one or more orientation detectors connected to at least one of the first measured article, the first imaging setup, the second imaging setup, and the reference object.

2. The method of claim 1, wherein the arranging of the one or more measured articles further comprises arranging one or more additional measured articles and the second imaging setup in such a way that the one or more additional measured articles are located in the visual field of the second imaging setup.

3. The method of claim 1, wherein the arranging of the one or more measured articles further comprises arranging one or more additional measured articles, the reflective surface and the first imaging setup in such a way that reflections of the one or more additional measured articles are located in the visual field of the first imaging setup.

4. The method of claim 1, wherein the calculating of the geometrical dimensions further comprises detecting a spatial orientation of at least one of the first imaging setup, the second imaging setup, the reference object, or the reflective surface.

5. The method of claim 1, wherein the calculating of the geometrical dimensions further comprises detecting spatial orientations of the one or more measured articles.

6. The method of claim 1, wherein the calculating of the geometrical dimensions further comprises calculating distances to the one or more measured articles.

7. The method of claim 1, wherein the first imaging setup comprises a front view imaging setup, and wherein the second imaging setup comprises a rear view imaging setup.

8. A system for measuring geometrical dimensions of one or more measured articles, comprising:
   a front view imaging setup;
   a rear view imaging setup;
   a reflective surface; and
   a reference object,
   wherein the front view imaging setup, the rear view imaging setup, the reflective surface and the reference object are arranged in such a way that a first measured article of the one or more measured articles is located in a visual field of the rear view imaging setup, with a reflection of the first measured article in the reflective surface and a reflection of the reference object in the reflective surface located in a visual field of the front view imaging setup.

9. The system of claim 8, wherein at least one additional measured articles of the one or more measured articles is located in the visual field of the rear view imaging setup.

10. The system of claim 8, wherein each reflection of at least one additional measured article of the one or more measured articles in the reflective surface is located in the visual field of the front view imaging setup.

11. The system of claim 8, wherein at least one of the front view imaging setup, the rear view imaging setup, the reflective surface, or the reference object is connected to a spatial orientation detector.

12. The system of claim 8, wherein each of the one or more measured articles is connected to a respective spatial orientation detector.

13. The system of claim 8, wherein the front view imaging setup and the rear view imaging setup are mounted in a single assembly.

14. The system of claim 8, wherein the front view imaging setup and the reference object are mounted in a single assembly.

15. The system of claim 8, wherein the rear view imaging setup and the reference object are mounted in a single assembly.

16. The system of claim 8, wherein the front view imaging setup comprises:
   an imaging device; and
   an imaging device mount on which the imaging device is mounted,
   wherein the imaging device mount is set to a front view position.

17. The system of claim 8, wherein the rear view imaging setup comprises:
   an imaging device; and
   an imaging device mount on which the imaging device is mounted,
   wherein the imaging device mount is set to a rear view position.

* * * * *